United States Patent
Schoenfeld

(10) Patent No.: US 6,740,037 B1
(45) Date of Patent: May 25, 2004

(54) HIGH FREQUENCY ULTRASONAGRAPHY UTILIZING CONSTRUCTIVE INTERFERENCE

(76) Inventor: Myron R. Schoenfeld, 7 Rochambeau Rd., Scarsdale, NY (US) 10583

( * ) Notice: Subject to any disclaimer, the term of this patent is extended or adjusted under 35 U.S.C. 154(b) by 0 days.

(21) Appl. No.: 10/315,737

(22) Filed: Dec. 10, 2002

(51) Int. Cl.⁷ .................................................. A61B 8/00
(52) U.S. Cl. ....................................................... 600/437
(58) Field of Search ................................. 600/407–471; 73/595–633; 367/7, 11, 130, 138; 128/916

(56) References Cited

U.S. PATENT DOCUMENTS

| | | |
|---|---|---|
| 4,222,274 A | 9/1980 | Johnson |
| 4,307,613 A | 12/1981 | Fox |
| 5,203,339 A | 4/1993 | Knuttel et al. |
| 5,938,612 A * | 8/1999 | Kline-Schoder et al. .... 600/459 |

* cited by examiner

*Primary Examiner*—Ali M. Imam
(74) *Attorney, Agent, or Firm*—Katten Muchin Zavis Rosenman

(57) ABSTRACT

Ultrasonic imaging utilizing high frequency ultrasound of 12 mHz in combination with constructive interference to increase the resolution of reflected images.

2 Claims, No Drawings

HIGH FREQUENCY ULTRASONAGRAPHY UTILIZING CONSTRUCTIVE INTERFERENCE

FIELD

Ultrasonic imaging utilizing high frequency ultrasound of 12 mHz in combination with constructive interference to increase the resolution of reflected images.

BACKGROUND

The invention of medical diagnostic ultrasonography itself was not due to the invention of a unique technique, but rather is a new application of existing knowledge. SONAR had been invented a decade earlier. In the early 1950's, Ehlers and Hertz of Sweden took an industrial ultrasound device "off-the-shelf" and tried it out on a human subject. Fortuitously, the ultrasound frequency of the device happened to be an appropriate one for humans, so that they were able to make a recording of the heart's mitral valve. All of the thousands of subsequent developments in medical ultrasonography emanate from here.

Sound can be represented as a sine wave caused by propagation of alternative phases of molecular compression and rarefaction. Sound has two important characteristics: intensity (loudness) and frequency.

The ultrasound beam progressively loses part or all of its energy as it travels through space and objects, a process called attenuation.

Ultrasound beams are not concordant, i.e., the crests and troughs of each of their constituent sub-beams are randomly distributed in time. As a result, many crests partially or completely are overlapped by troughs, thereby partially or completely canceling them out. Consequently, reflected beams are much weaker than they could be if they were concordant. Thus, discordancy results in decreased image resolution.

A medical ultrasound machine consists of two components: a small, freely mobile, hand-held transducer, and a large, but portable, console. The transducer is that device which is held against the skin or other accessible body surface of the patient to send and receive the ultrasound signals. The console processes the ultrasound signals by various kinds of complex electronic circuitry, for real time display on a cathode ray screen, and on video printer paper for detailed analysis and hard copy permanent record keeping, The transducer is tethered to the console by a flexible electric cable.

The transducer includes a circular (or other) array of multiple ultrasound transmitters (crystals) which create (and receive) converging ultrasound beams at the target organ, just like the ribs of an umbrella converge at the umbrella's distal end. The depth of convergence (focus) is determined manually (steered) by the examining physician or technologist, depending on the depth of the organ being investigated, and the superimposition of the crests is done automatically by a computer.

Medical ultrasonography utilizes reflected (echo) ultrasound, rather than transmitted ultrasound. In this way, it is like radar, and unlike x-ray radiography. Ultrasound, like electromagnetic radiation, undergoes transmission, absorption, scatter and reflection in the body. Attenuation results from absorption and scatter. Medical ultrasound transducers incorporate both the transmitting and receiving crystals. There are no biological ill-effects from medical ultrasonography, unlike x-ray studies.

The higher the ultrasound frequency, the greater the detail (resolution) of the image, but the greater the attenuation, and the less the depth of penetration. As a result, deep structures are visualized only faintly or not at all by high frequency ultrasound transducers.

On the other hand, lower frequency ultrasound can penetrate deeper, but its images lack fine detail (poorer resolution).

Because of the higher degree of attenuation of high frequency sound and the lower resolution of low frequency ultrasound, sound imaging of deep structures in the human body, like the heart and most abdominal organs, and particularly in large people, is not capable of providing the maximum degree of clarity desired by medical diagnosticians.

Current medical diagnostic ultrasound systems use low fundamental carrier frequencies in the range of 2.0–3.5 mHz to visualize the deep-lying viscera of the chest, abdomen, and pelvis. In recent years, manufacturers have used computer amplification to capture and record the second harmonics of echoing ultrasound beams in order to increase image resolution.

Theoretically, the penetrability of high frequency ultrasound could be increased by increasing its energy (loudness) just by turning up the wattage. Unfortunately, such high energy, high frequency ultrasound can cause skin burns and chromosome damage in the skin and/or internal organs. Hence, this option is not available for use in biological systems.

Digitization, the use of color rather than a gray scale, intravenous contrast agents, and other techniques also recently have been introduced to improve image resolution.

The only other known way to increase ultrasound penetration is by the recently described SASER. This device is the sound counterpart of the LASER, and depends on magnifying sound by a kind of ricocheting chain-reaction similar to what happens to light in the LASER machines. If it worked well, it too would be expected to cause skin burns and chromosomal damage for the same reasons as noted with respect to high energy, high frequency ultrasound. To date, it does not work that well, magnifying sound only up to 50%. Furthermore, present SASERs require temperatures far below zero. Hence, SASERs do not have any biological applicability at present.

LASERS and MASERS use constructive interference of light and microwaves respectively for their own special purposes. Similarly, noise cancellation technology patents employ sound destructive interference for their specific application.

Johnson, U.S. Pat. No. 4,222,274, dated Sep. 16, 1980, entitled Ultrasonic Imaging Apparatus and Method, the disclosure of which is incorporated herein by reference, is an early patent which discloses an ultrasound imaging apparatus which utilizes the principle of constructive interference to enhance the signal strength of a reflected wave. In this particular patent, constructive interference is obtained by transmitting a particular waveform—which has the characteristic of a high amplitude center lobe with symmetrical low amplitude side lobes.

Fox, U.S. Pat. No. 4,307,613, dated Dec. 29, 1981, entitled Electronically Focused Ultrasound Transmitter, discloses a transmitter for use in an ultrasound apparatus that comprises an annular array of transducer elements which are arranged such that the emitted acoustic waves constructively interfere at an electronically controlled focal point. This patent is not concerned with the reflected wave, but does teach the benefit of constructive interference for enhancement of the transmitted wave at the point to be imaged. It also teaches the use of an annular array having multiple transducers.

Perhaps the best exposition of the utilization of constructive interference for the enhancement of signal strength is found in Knuttel, et al., U.S. Pat. No. 5,203,339, dated Apr. 20, 1993 and entitled Method and Apparatus for Imaging a Physical Parameter in Turbid Media Using Diffuse Waves. Knuttel discusses the benefits of constructive interference appurtenant to the use of light photons/waves, and goes into some detail regarding improved signal resolution without the need to increase the amplitude of the transmitted wave.

There are other patents relate to the benefits of constructive interference in enhancing transmitted or received acoustic waves.

In sum, the broad idea of utilizing constructive interference in an ultrasound imaging apparatus is well known.

Several companies already manufacture noise-dampening devices based on the reverse of the amplification principle described above. The devices emit sound which is synchronized by digital computers to be out of phase with the noise, so that their respective crests and troughs overlap and thereby cancel themselves out.

Diagnostic medical ultrasound equipment was first invented in the 1950s. Many advances have been made since then. Many current medical diagnostic ultrasound systems employ the principle of constructive interference with low frequency ultrasound transducers to help improve the rather poor image resolution of deep lying structures when interrupted by low frequency ultrasound.

However, no current technique has been able to achieve the degree of resolution desired by and necessary to bring the full fruits of ultrasound imaging to medical diagnostics. For unknown reasons, no one has thought to combine constructive interference with high frequency ultrasound to achieve a unique combination of advantages not otherwise obtainable in medical imaging.

Thus, there exists a continuing need for a high resolution ultrasound diagnostic system that is uncomplicated and simple to use.

DESCRIPTION OF THE INVENTION

The present invention achieves high levels of resolution to medical diagnostics by combining high frequency ultrasound and constructive interference.

The fundamental physical principle underlying constructive interference is the synchronization of multiple single-frequency (and hence wave-length) sound waves so that their crests and troughs overlap. This principle can be termed Sound Amplification by Wave Synchronization (SAWS), or, more technically, Sound Amplification by Constructive Interference Re-inforcement (SACIR).

The SAWS high frequency ultrasound (approx. 12 mHz for deep-lying structure] transducer system greatly increases image resolution of deep-lying bodily structures, while the constructive interference of this ultrasound greatlys increase its amplitude and thereby its depth of penetration and, hence, the perception of these structures. In this way, there results a combination of the advantages of both high and low frequency ultrasound without the disadvantages of either.

The frequencies used in the SAWS system can be contrasted with conventionally used frequencies, which are as follows:

2.0–3.5 mHz for the deep lying structures (viscera) in the chest, abdomen, and pelvis of adults. These structures include the heart, liver, spleen, kidneys, aorta, pancreas, gall bladder and bile ducts, bladder, uterus, and ovaries. This use comprises the great majority of ultrasound procedures.

7.5 mHz for the superficial "small parts" of adults, such as the thyroid, testes, breast masses, and the arteries and veins of the neck and limbs.

5.0–10.0 mHz for babies and young children.

By comparison, the "high frequency ultrasound." utilized in the SAWS ultrasound system is significantly higher [approx. 12 mHz] than the conventionally used frequencies for deep lying structures [2.0–3.5 mHz].

The SAWS ultrasound system depends on three principles:

1] Ultrasound is progressively attenuated as it progressively passes forward from the transducer to the target organ and then is reflected back to the transducer and finally to the ultrasound machine for imaging;

2] Constructive interference (superimposing crests and troughs) magnifies the intensity of ultrasound, and, thereby, increases its ability to be perceived; and 3] The higher the ultrasound frequency (and the shorter the wavelength) the greater the image resolution, but the less the depth of penetration, and vice versa.

Many discrete, narrow beam, high frequency ultrasound emitters are incorporated into the SAWS transducer. These individual elements can be arranged in a circular or linear array or in other configurations to meet special requirements; different arrays may be needed for different kinds of studies. Circular arrays are most commonly used. In a circular array transducer, the elements are arranged in concentric circles. In a linear array, they are arranged in parallel rows to form an oblong rectangle. Linear array transducers are primarily used in abdominal and pelvic, and particularly in obstetrical examinations where the doctor requires a wider image. The technique of utilizing constructive interference applies to both arrangements of transducers.

With each transducer, each of the ultrasound-emitting elements will be focused at the same distance but the focal length will vary from transducer to transducer depending on the depth of the internal organ of interest. Phase synchronization of the emitting elements within each transducer will be accomplished by digital computer, so that crests overlap crests.

The waves of the ultrasonic transducer remain parallel for a certain distance known as the "near field" after which they begin to diverge in what is called the "far field". This divergence decreases resolution, thereby blurring the image and needs to be counteracted by a focusing means. The length of the near field is directly proportional to the square of the radius of the transducer, inversely proportional to the wavelength of the ultrasound and therefore directly proportional to the ultrasound frequency. Thus, for a 12 mm diameter circular array transducer, a 2.25 mHz transducer has a near field length of 5.26 cm, while a 5.0 mHz transducer has a near field length of 11.6 cm.

In this manner, only the target organ will receive the amplified sound, so that skin and intervening tissue are not overdosed with ultrasound, and, therefore, are not damaged.

At the focal point, the target organ, the high frequency ultrasound arrives markedly attenuated, but there it is markedly amplified so that the reflected beams arrive back at the transducer and ultrasound recorder in detectable quantities.

In these ways, the SAWS transducer achieves the detailed image resolution characteristic of high-frequency ultrasound interrogation, and the depth of penetration of low-frequency ultrasound interrogation—without the biological risks entailed by greatly increasing the electrical power output of the ultrasound machine.

There is a very serious, and sometimes fatal, illness known as bacterial endocarditis in which germs start growing on the heart's valves, damaging the valves and spewing germs throughout the body. Obviously, the sooner this disease is diagnosed and treated with antibiotics, the better. However, because in the early stages the symptoms of this terrible disease are subtle, an important means for confirmation of the diagnosis is echocardiography to visualize the colonies of germs ("vegetations") growing on the heart valves, Presently, utilizing conventional 2.0–2.5 mHz transducers, these vegetations can be visualized only when they reach the size of about 2 mm.

Using the disclosed invention, and the increased resolving power inherent therein, these vegetations can be visualized at a fraction this size, treatment can begin at an earlier stage and morbidity and mortality can be significantly reduced.

Capturing and recording the second harmonics of the echoing ultrasound beam yields even greater resolution. Since the second harmonic wavelengths are half those of the fundamental wavelengths [first harmonics] the image resolution of the harmonics will be sufficient to open new fields of application for medical ultrasonography.

The purpose of the SAWS medical ultrasound transducer and system is to greatly improve the resolution of medical ultrasonography images, and, thereby, improve the diagnostic sensitivity for identifying presently invisible objects (e.g., tiny tumors) and better delineating the borders of presently identifiable, but poorly delineated, objects (e.g., the lining of the heart). The achievement of both of these objectives will significantly improve medical care.

What is claimed is:

1. A high resolution medical ultrasonography diagnostic method for the imaging of deep lying structures within the body of a patient comprising providing an array of discrete, narrow-beam high frequency tranducers having a frequency of at least 12 mHz;

phase synchronizing the multiple single-frequency ultrasonic beams produced by the transducers so that their crests and troughs overlap;

applying the transducer array to the a portion of the patients body near the deep lying structure to be imaged;

initiating and transmitting ultrasound energy signals;

receiving reflected ultrasound energy signals;

electrically receiving and storing the received ultrasound signals;

combining the stored signals so as to reconstruct the image of reflection corresponding to the scanned deep lying structures; and displaying the reconstructed image of reflection.

2. In a method of imaging the internal structure of a patient utilizing an ultrasound imaging apparatus to reconstruct images of scanned deep lying structures by analyzing reflected ultrasound energy where such apparatus comprises means for transmitting multiple single-frequency ultrasound energy signals to the internal structure of the patient;

means for receiving reflected ultrasound energy signals;

means for storing the received ultrasound signals;

means electronically connected to the storage means for combining the stored signals so as to reconstruct the image of reflection corresponding to the scanned deep lying structures; and means for displaying the reconstructed image of reflection the improvement comprising increasing the resolution of the image utilizing ultrasound frequencies in the range of 12 mHz or greater in combination with constructive interference.

* * * * *